United States Patent [19]

Holtkamp, Sr.

[11] Patent Number: Plant 7,661

[45] Date of Patent: Oct. 1, 1991

[54] AFRICAN VIOLET PLANT NAMED LITTLE RHODONITE

[76] Inventor: Reinhold Holtkamp, Sr., Blumenstrasse 28, D 4242 Rees-Haffen, Fed. Rep. of Germany

[21] Appl. No.: 551,737

[22] Filed: Jul. 12, 1990

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner

[57] ABSTRACT

A new and distinct cultivar of African violet named Little Rhodonite characterized by its miniature growth habit; single to semi-double, pink flowers with elongated petals; strong stems which curve toward the center to form a compact bouquet above the leaves; profuse and continuous flowering; medium green, heart-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Rhodonite.

The new cultivar was referred to during the breeding and selection process by the designation K/1/68 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated 43.

Little Rhodonite was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Phodonite has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Rhodonite, which in combination distinguish this African violet as a new and distinct cultivar:

(1) Little Rhodonite will not grow taller than 7–8 cm.

(2) Single to semi-double pink flowers with elongated petals.

(3) Strong wirelike and upright flower stems curving toward the center.

(4) First flash of flowers form a tight bouquet above the leaves.

(5) Profuse flowering; under good growing conditions continuous flowering.

(6) Each plant carries 9–11 and more upright flower stems each of which carries 6–7 and more flowers.

(7) Long lasting, non-dropping flowers.

(8) Plant Saleable 10 to 11 weeks after planting of unrooted shoot.

(9) Seed capsules push slightly through.

(10) Medium green, hairy leaves.

(11) Heart-shaped leaves are 2.4 to 2.8 cm in size.

(12) After maturity the flowers dry off, and remain on the peduncle.

The new cultivar is most similar to Little Tourmaline, disclosed in U.S. Plant Pat. No. 7,102. Similarities are the flower shape and Group color. However, Little Rhodonite has a lighter pink color and single to semi-double blooms, whereas Little Tourmaline always has semi-double blooms and even more elongated petals than Little Rhodonite.

The accompanying color photographic drawing shows a typical specimen plant of the new cultivar grown in a 4 cm pot. The plant is pictured next to a pencil, highlighting the miniature size and growth habit of Little Rhodonite. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Little Rhodonite.

Parentage:

*Male parent.*—43.

*Female parent.*—4 Mini.

Propagation: The new cultivar holds its distinguishing characteristics through successive propagations by leaf cuttings.

Plant: From 7 cm to 8 cm tall when grown in pots, and approximately 8–9 cm in diameter when fully grown.

Leaves:

*General form.*—Heart-shaped.

*Diameter.*—20–25 mm wide and 22–27 mm long.

*Texture.*—Leatherlike.

*Aspect.*—Shiny, hairy.

*Veins.*—Upperside: visible; underside: well pronounced, light green, shiny.

*Color (upperside).*—Yellow-Green Group 147 A.

*Color (underside).*—Yellow-Green Group 147 D, young leaves are Greyed-Purple Group 186 B.

*Petiole.*—Strong, green with reddish brown touch, hairy.

Flowers:

*Buds.*—Size: 4–5 mm just before opening. Shape: Bell-shaped. Color: Pinkish green.

*Sepals.*—Five (5). Color: Brownish green.

*Calyx.*—Shape: Funnel-shaped. Aspect: Spear-shaped, hairy.

*Peduncle.*—Character: Strong upright, hairy. Color: Brownish green.

*Individual flowers.*—Size: 22–25 mm. Shape: Violet-shaped, single to semi-double (having up to 10 petals). Color (upperside): Purple Group 78 C to D, center 78 B. Under cooler temperatures and more intensive lighting, the pink tends to intensify. Color (underside): Purple Group 78 D. Borne: Each flower stem carries 6–7 and more flowers on strong, upright peduncle that are free standing above the leaves, thereby forming a compact bouquet. Flowering habit: Flowers 10–11 weeks after planting an unrooted plantlet.

Reproductive organs:

*Stamens.*—One to two (1–2). Anthers: 1–2 composed of 2–4 anther cells, seed capsule pushes slightly through.

*Filaments.*—Greenish white, 3–4 mm long.

*Styles.*—5–6 mm long, pink, base of ovary light green and hairy.

Roots: Normally developed, white when young, turning slightly brownish when older.

Disease resistance: Good.

General observations: Little Rhodonite is a super miniature violet, which does not grow taller than 7–8 cm. The pink, single to semi-double flowers have up to 10 elongated petals. The anthers may be covered up by the little petals in the center. The flowers are long-lasting and non-dropping. Under good growing conditions, Little Rhodonite will bloom continuously. A nice bouquet of flowers free standing above the medium green, heart-shaped leaves develops approximately 10–11 weeks after planting an unrooted plantlet. Each of the 9–11 and more strong flower stems carries 6–7 and more flowers.

I claim:

1. A new and distinct cultivar of African violet named Little Rhodonite, as described and illustrated, and particularly characterized by its miniature growth habit; single to semi-double, pink flowers with elongated petals; strong stems which curve toward the center to form a compact bouquet above the leaves; profuse and continuous flowering; medium green, heart-shaped leaves; flowering 10–11 weeks after planting of unrooted shoot, and by its long lasting and non-dropping flowers.

* * * * *

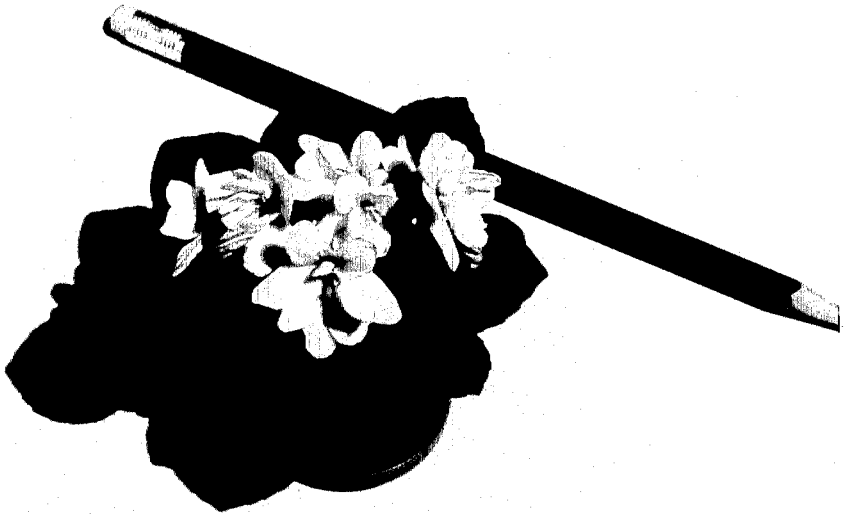
1